(12) United States Patent
Evans et al.

(10) Patent No.: US 6,344,556 B1
(45) Date of Patent: Feb. 5, 2002

(54) POLYMERISABLE MONOMERS AND POLYMERS

(75) Inventors: Richard Alexander Evans, Clayton; Ezio Rizzardo, Wheelers Hill; Graeme Moad, Kallista, all of (AU)

(73) Assignee: Commonwealth Scientific and Industrial Research Organisation, Campbell (AU)

(*) Notice: Subject to any disclaimer, the term of this patent is extended or adjusted under 35 U.S.C. 154(b) by 0 days.

(21) Appl. No.: 09/208,761

(22) Filed: Dec. 10, 1998

Related U.S. Application Data

(62) Division of application No. 08/849,529, filed as application No. PCT/AU95/00859 on Dec. 18, 1995, now Pat. No. 6,043,361.

(30) Foreign Application Priority Data

Dec. 22, 1994 (AU) .......................... PN0232/94

(51) Int. Cl.[7] ............................ C07D 267/22
(52) U.S. Cl. ...................... 540/467; 549/10; 549/11; 549/20
(58) Field of Search ............. 540/467; 549/10, 549/11, 20

(56) References Cited

FOREIGN PATENT DOCUMENTS

WO 94/14792 7/1994

OTHER PUBLICATIONS

"Functionalized Thia Crown Ethers", Buter et al, J. Chem. Soc., Chem. Commun., (1990), (3). 282–4, Dec. 1990.*
Richter, Z. CHEM, S. Jg., pp. 220–221 (1968).
Tostikov et al., Z. Org. Khim., 1986, 22(7), 1261–6.
Martinez et al., Z. Chem., 1978, 18(2), 61–2.
Dietrich et al., DD–100001–A, Sep. 5, 1973.
Edema et al.: "A Simple One–Step Synthesis of Symmetrical Thiocrown Ethers . . . ", Angew. Chem., vol. 32, No. 3, 1993, pp. 436–439, XP002053340, see p. 437, compound 3c.
Evans R.A. et al.: "Free Radical Ring–Opening Polymerization of Cyclic Allylic Sulfides", Macromolecules, Vo. 29, No. 22, Oct. 21, 1996, pp. 6983–6989, XP000629330.

* cited by examiner

*Primary Examiner*—Bernard Lipman
(74) *Attorney, Agent, or Firm*—Bacon & Thomas

(57) ABSTRACT

The invention relates to compounds of the formulae:

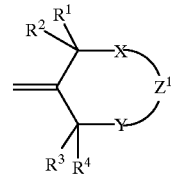

Formula 1a

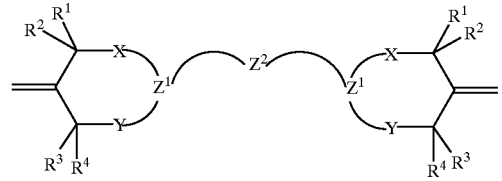

Formula 1b processes for their preparation, polymers, co-polymers or block co-polymers containing them or their use as monomers or co-monomers in free radical polymerisation and in the manufacture of adhesives, dental composites or optical lenses.

1 Claim, No Drawings

POLYMERISABLE MONOMERS AND POLYMERS

This application is a divisional application of pending U.S. patent application Ser. No. 08/849,529, filed Aug. 26, 1997, now U.S. Pat. No. 6,043,361 which is the National Stage of PCT application PCT/AU95/00859, filed Dec. 18, 1993 and which application has issued as U.S. Pat. No. 6,043,361.

The invention relates to new unsaturated cyclic organic compounds which can be used as monomers or co-monomers in free radical polymerisation and polymers or co-polymers derived from these compounds. These compounds have the ability to ring open during polymerisation and provide examples of allylic monomers that will readily polymerise to high molecular weight polymers.

Monomers capable of ring opening (hereinafter referred to as "ring-opening monomers") are important in minimising volume shrinkage during polymerisation. Additionally, ring-opening monomers are useful in providing an alternative method of incorporating functionalities such as amide, ester or carbonate into the backbone of a polymer. Generally, such functionalities are introduced by step growth (i.e. poly esterification) polymerisation rather than chain growth (i.e. free radical and ionic) polymerisation. The limitations of step growth polymerisation are that (a) very high conversion is required for high molecular weight polymers and (b) elimination products, such as, water or HCl are formed and require removal. In contrast, chain growth polymerisation results in very high molecular weight polymers from the beginning of the polymerisation.

There are many types of ring-opening monomers available for ionic polymerisation. However, there are only a limited number of ring-opening monomers available for free radical polymerisation. A review by Endo et al. in Chapter Five of *New Methods for Polymer Synthesis,* Plenum Press, New York, 1992 summarises the present state of the art. The major types of free radical polymerisation ring-opening monomers are vinyl cyclopropanes, cyclic vinyl ethers, cyclic ketene acetals (U.S. Pat. No. 4,857,620) spiro ortho esters and Spiro ortho carbonates.

Many of these known ring-opening monomers suffer from limitations. Ring opening of the vinyl cyclopropanes is a reversible process and substituents that favour ring opening may also inhibit polymer growth by excessive stabilisation of the ring-opened propagating radical. The oxygenated ring-opening monomers can also exhibit sensitivity to trace amounts of acid. This results in difficulties with their synthesis and subsequent storage. Furthermore, ring opening is not guaranteed and the final polymers can contain various proportions of opened and unopened rings. In addition, the Spiro ortho esters and spiro ortho carbonates have the following problems as described in *Expanding Monomers,* Eds. Sadhir, R. K. and Luck, R. M., CRC Press, Boca Raton,1992:

(i) They are sensitive to impurities. Impurities can prevent ring opening from occurring and make the polymerisation somewhat irreproducible.

ii) They have a low reactivity towards free radical polymerisation. This is partly due to side reactions, such as degradative chain transfer, in the polymerisation of allylic monomers.

iii) They have a low reactivity ratio with common commercial vinyl monomers, such as, styrene, methyl methacrylate and other monomers having a similar reactivity.

iv) They are crystalline compounds with low solubilities in organic solvents and monomers.

International Patent Application No. PCT/AU93/00667 discloses new cyclic acrylate monomers which undergo facile ring opening. These compounds are readily co-polymerised with monomers that co-polymerise with acrylates or styrenic monomers.

Some compounds within the scope of the present invention have been previously reported in the following references:

(1) Butler, J.; Kellogg, R. M.; van Bolhuis, F., "Functionalized Thia-crown Ethers. Synthesis, Structure and Properties.", *J Chem Soc., Chem Comm.,* 1990, 282;

(2) Tostikov, G. A.; Kanzafarov.F,Ya.; Kanzafarova, S. G.; Singizova, V. Kh., "Nucleophilic Thialation of Allyl Halides in the Presence of Phase-Transfer Catalysts"., *Z. Org. Khim,* 1986, 22(7), 1400;

(3) Martinetz, D.; Hiller, A. "Phase Transfer-Catalytic Conversion of Unsaturated Organic Halogen Compounds with Sodium Sulfide Nonahydrate.", *Z. Chem.,* 1978, 18(2), 61;

(4) Dietrich, E-M.; Schulze, K.; Muhlstadt, M., "1,5-Dithiacyclanes", East German Patent No. 100 001., Sep. 5, 1973; and (5) Richter, H.; Schulze, K; Muehlstaedt, M., "Reactions of 1,3-Dichloro-2-methylenepropane", *Z Chem.,* 1968, 8(6), 220.

References (1) to (5) are sparse in detail other than stating that the compound was made, together with a brief description of its synthesis. The use of these monocyclic monomers in free radical polymerisation is not disclosed in these references.

We have now found new unsaturated cyclic organic compounds which are capable of undergoing free radical polymerisation. These compounds include monocyclic compounds and bicyclic compounds in which two monocyclic units are tethered together.

Allylic monomers, such as allyl acetate, generally polymerise slowly, with a low degree of conversion and low molecular weight oligomers being formed. This is largely due to the occurrence of extensive degradative chain transfer during the polymerisation.

Some of the monocyclic compounds have been previously made and reported as discussed above, but their use in free radical polymerisation has not previously been disclosed. The cyclic compounds of the present invention avoid the degradative chain transfer problems of allylic monomers by converting the initially highly reactive, non-selective carbon-centered radical into a less reactive, more selective sulfur-centered radical by rapid ring-opening.

The bicyclic compounds are new and the use of such compounds is in the replacement of conventional bi-functional monomers, such as, CR 39 and dimethacrylates. Thus, crosslinked polymers may be produced with significantly less shrinkage. According to one aspect of the present invention there is provided compounds of the formulae:

Formula 1a

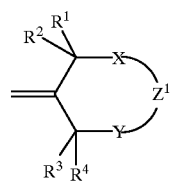

-continued

Formula 1b

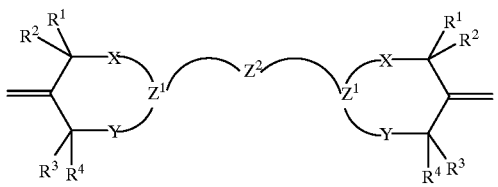

wherein:
$R^1$ to $R^4$ may be the same or different and are selected from hydrogen, halogen, optionally substituted alkyl, optionally substituted aryl, nitrile, hydroxy, alkoxy, acyloxy and ester; or $R^1$ and $R^2$ or $R^3$ and $R^4$ together form methylene;

X is selected from sulfur, sulfoxide, sulfone and disulfide;

Y is selected from sulfur, oxygen $SO_2$, N—H, N-alkyl, N-aryl, acyl and $CR^5R^6$ wherein $R^5$ and $R^6$ are the same as $R^1$ to $R^4$; and $Z^1$ and $Z^2$ are linking functionalities.

The compounds of Formula 1a wherein $R^1$ to $R^4$ are hydrogen, X and Y are sulfur and $Z^1$ is —$(CH_2)_2$— or —$CH_2$—$C(=CH_2)$—$CH_2$— are known per se and therefore excluded from the compounds of the present invention.

Preferably X is S or $SO_2$ and Y is $C(R^5R^6)$, S, O or $SO_2$.

Suitable linking functionalities for $Z^1$ include —$(CRR)_n$—, —$(CRR)_n$—O—(CO)—O—$(CRR)_m$—, —$(CRR)_n$—O—(CO)—$(CRR)_m$—, —$(CRR)_n$—O—$(CRR)_m$—, —$(CRR)_n$—$C(=CH_2)$—$(CRR)_m$—, —$(CRR)_n$—CO—$(CRR)_m$—, —$(CRR)_n$—$(C=O)$—, —$(CRR)_n$—S—$(CRR)_m$—, —$(CRR)_n$—$SO_2$—$(CRR)_m$—, —$(CRR)_n$—S—S—$(CRR)_m$—, —(O—CRRCRR)$_n$— and optionally substituted phenyl (wherein R may vary within the linking functionality and is preferably selected from hydrogen, alkyl, haloalkyl, hydroxyalkyl, hydroxy, carboxy, optionally substituted phenyl, halogen and $Z^2$; and m and n are integers including zero).

Suitable linking functionalities for $Z^2$ in the compounds of the Formula 1b include —G—$(CRR)_p$—J—, —G—$(CRR)_p$—O—(CO)—O—$(CRR)_q$—J—, —G—$(CRR)_p$—O—(CO)—$(CRR)_q$—J—,—G—$(CRR)_p$—O—$(CRR)_q$—J—, —G—$(CRR)_p$—$C(=CH_2)$—$(CRR)_q$—J—, —G—$(CRR)_p$—CO—$(CRR)_q$—J—, —G—$(CRR)_p$—$(C=O)$—J—,—G—$(CRR)_q$—S—$(CRR)_p$—J—,—G—$(CRR)_p$—$SO_2$—$(CRR)_q$—J—,—G—$(CRR)_p$—S—S—$(CRR)_q$—J—, —G—(O—CRRCRR)$_p$—J—and optionally substituted phenyl (wherein R may vary within the linking functionality and is preferably selected from hydrogen, alkyl, haloalkyl, hydroxyalkyl, hydroxy, carboxy, optionally substituted phenyl and halogen; G and J are functional groups which join $Z^2$ to $Z^1$ and may be selected from a bond, —$(CRR)_r$—, —O—, NH—, —S—, —$(C=O)O$—, —O—$(C=O)O$—, —$(C=O)NH$—, —NH—$(C=O)$—O—; and p, q and r are integers including zero). Thus, $Z^2$ can be derived from di-functional compounds capable of reacting with a functional group, such as, hydroxy, aldehyde, ketone and carboxy from the cyclic portion of the compounds of the Formula 1a. Suitable difunctional compounds from which $Z^2$ could be derived, include diols, for example, pentane diol; dithiols; diamines; diacids, for example, succinic and phthalic acids; dichlorosilanes, for example, dichlorodimethylsilane; diisocyanates, for example, hexamethylene diisocyanate and toluene diisocyanate; and α-ω hydroxy acids.

In the above definitions, the term "alkyl", used either alone or in compound words such as "haloalkyl" and "hydroxyalkyl" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3-, or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7-, or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "halogen" denotes fluorine, chlorine, bromine or iodine, preferably chlorine or fluorine.

The term "aryl" denotes single, polynuclear, conjugated and fused residues of aromatic hydrocarbons or aromatic heterocyclic ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl, pyridyl, 4-phenylpyridyl, 3-phenylpyridyl, thienyl, furyl, pyrryl, indenyl, pyriazinyl, pyrazolyl, pyrazinyl, thiazolyl, pyrimidinyl, quinolinyl, isoquinolinyl, benzofurnayl, benzothienyl, purinyl, quinazolinyl, phenazinyl, acridinyl, benoxazolyl, benzothiazolyl and the like.

The term "acyl" either alone or in compound words such as "acyloxy" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexyl-carbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio and phosphorus-containing groups.

Representative examples of the compounds of the invention wherein n is as defined above are as follows:

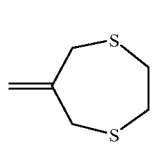
1a-1

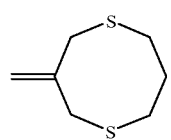
1a-2

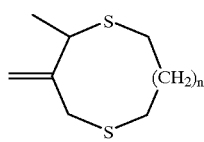
1a-3

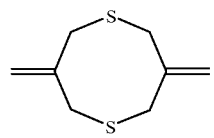
1a-4

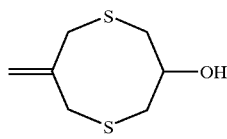
1a-5

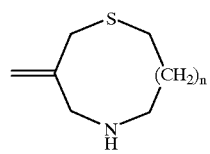
1a-6

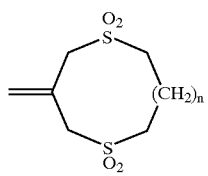
1a-7

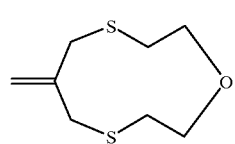
1a-8

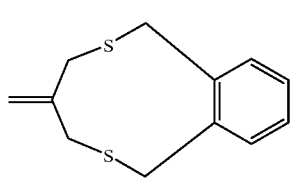
1a-9

1a-10

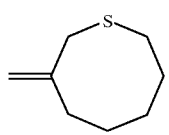
1a-11

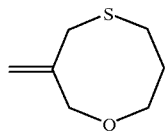
1a-12
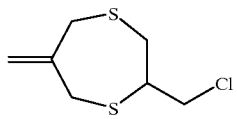
1a-13
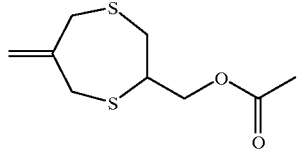
1a-14
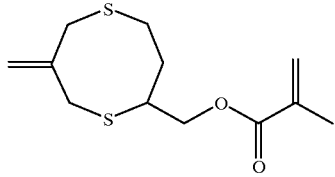
1a-15
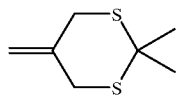
1a-16
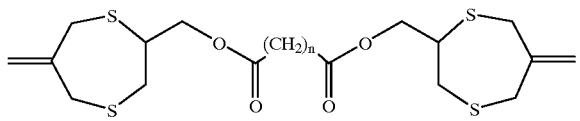
1b-1
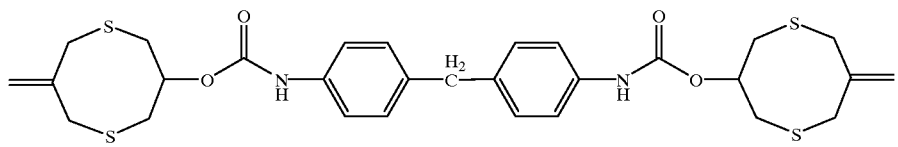
1b-2
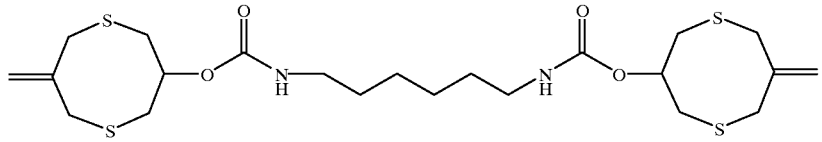
1b-3
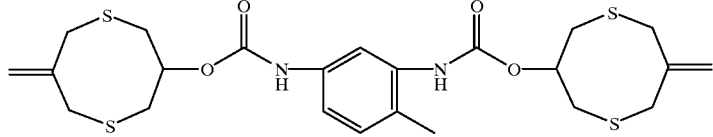
1b-4
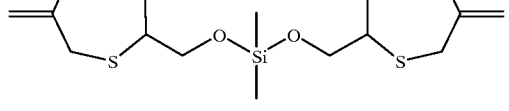
1b-5
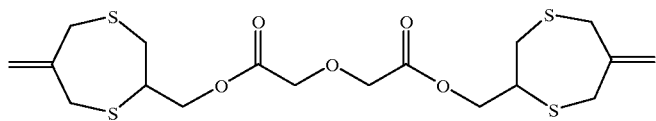
1b-6
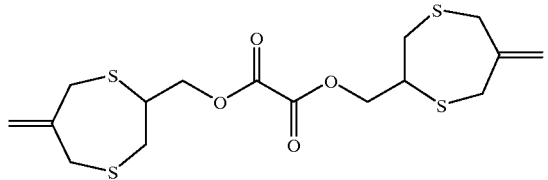
1b-7

1b-8
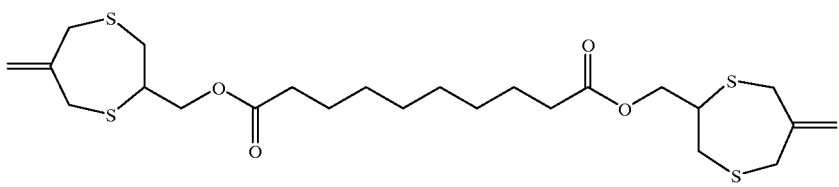

1b-9
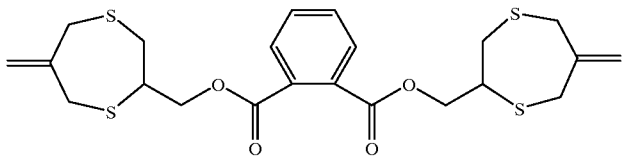

1b-10
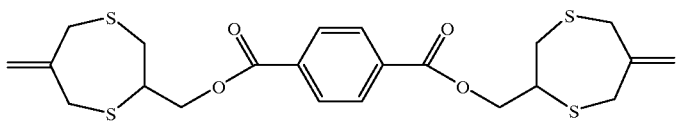

1b-11
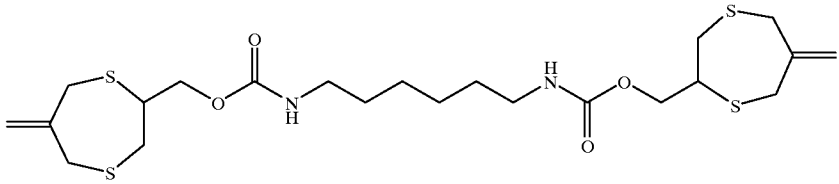

1b-12
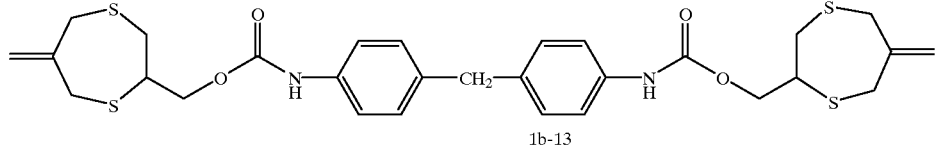

1b-13
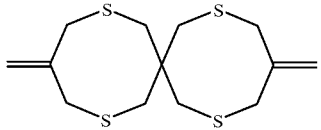

1b-14

According to another aspect of the present invention there is provided a polymer or co-polymer which is derived from at least one monomer of the Formula 1a and/or 1b.

The present invention also provides a co-polymer derived from at least one monomer of the Formula 1a and/or 1b and at least one monomer selected from unsaturated compounds susceptible to free radical polymerisation.

Suitable unsaturated compounds include acrylic esters or amides, vinyl esters, vinyl aromatics, olefins or dienes.

The present invention further provides the use of compounds of the Formula 1a and/or 1b as monomers or comonomers in free radical polymerisation.

The compounds of the Formula 1a and/or 1b may be used as monomers or co-monomers in free-radical homo- or co-polymerisations. The polymerisations may be carried out in bulk or in solution. The compounds may be co-polymerised with each other or with other monomers having a suitable reactivity, such as, for example, those monomers listed in *The Polymer Handbook,* Ed Brandup. The polymerisation may be initiated by any suitable known method such as, redox; photochemical, for example, camphor quinone/aromatic amine or "Darocur 1173" by Ciba-Giegy; or thermal (i.e. AIBN) methods.

The compounds of the invention possess the ability of being able to ring open efficiently during free radical polymerisation. They undergo essentially 100% ring opening. Unlike other allylic compounds, these compounds readily polymerise to high molecular weight polymers.

In a polymerisation process, the monomers of the Formulae 1a will ring open by undergoing β-bond cleavage in the manner shown in Scheme 1 below using a monomer of the Formula 1a–1 as defined above. Similarly, the di-functional, bicyclic monomers of the Formula 1b will undergo dual ring opening to give a cross-linked network.

Scheme 1

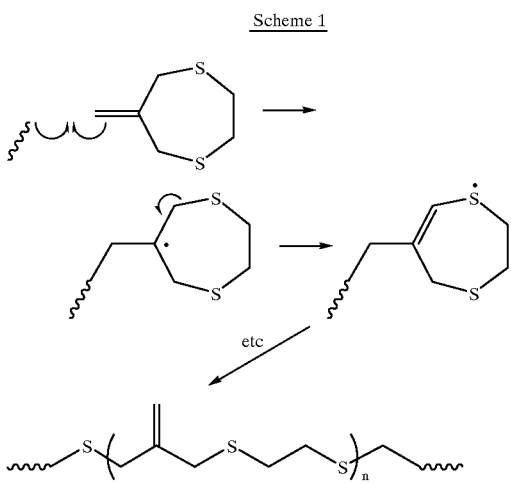

Generally, polymers and co-polymers resulting from a process involving the compounds of the invention will contain the compounds of the Formula 2a and/or 2b, respectively as repeating units as shown in Scheme 2 below.

glass transition at 47.5° C. Furthermore, a co-polymer of methyl methacrylate and a monomer of the Formula 1a–1 (16:1) shows essentially no crystallinity. Thus, the mechanical properties of polymers made using monomers of the Formula 1a and/or 1b can be varied as required.

The compounds of the invention enable the production of polymers having structures not otherwise obtainable. The presence of a methylene group in a polymer formed by free radical polymerisation allows a wide scope for further processing of the polymer. By way of example, the methylene group can be used as a point of further chemical manipulation. The manipulation could be in the form of standard addition chemistry to the carbon-carbon double bond or the active methylene unit could be used as a point of grafting or crosslinking. This crosslinking could occur during polymerisation or on the final co-polymer as a separate step.

Under the appropriate conditions, homopolymers of the compounds may undergo depolymerisation. For example, the homopolymer of the Formula 1a–1 depolymerises to monomers if heated to ca. 130° C. in dimethyl sulfoxide. This facility for depolymerisation wood allow, for example, the synthesis of block co-polymers if the homopolymers were Heated for example in DMSO in the presence of another monomer such as methyl methacrylate.

Scheme 2

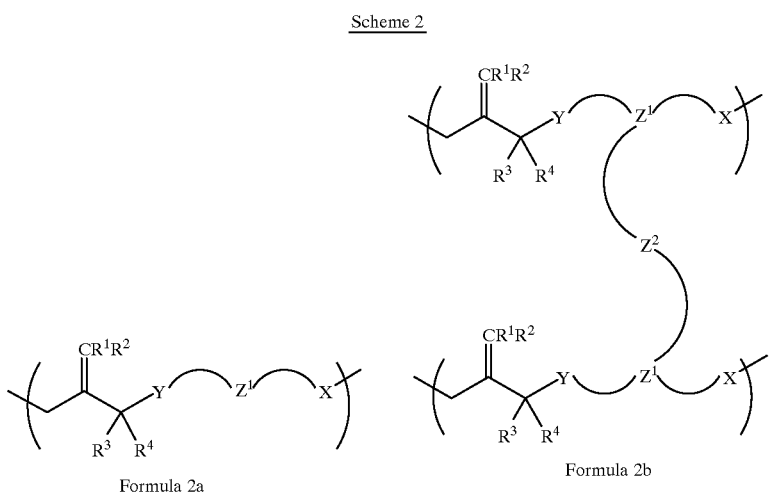

Formula 2a

Formula 2b

The polymerisation process of the invention allows the manufacture of polymers with a wide range of functionalities in and attached to the polymer backbone. Such polymers are generally made by step growth polymerisation which requires that the polymerisation be taken to a very high conversion in order to obtain high molecular weights. By using the compounds of the invention alone in free radical polymerisation or as co-monomers in co-polymerisations, polymers may be prepared having controlled amounts of the repeating unit of Formula 2.

By choosing appropriate substituents and co-monomers, the monomers of the Formula 1a and/or 1b can produce polymers with a degree of crystallinity ranging from high to essentially no crystallinity. For example, a homopolymer derived from a monomer of the Formula 1a–1 forms a white crystalline polymer with a melting point of 129° C. and a very small glass transition at −35° C., but a co-polymer derived from monomers of the Formula 1a–1 and/or 1a–2 (1:1) is a white rubber like solid with a much smaller observed melting point occurring at −53.3° C. and a marked Thus, according to a further aspect of the present invention there is provided a process for the preparation of a block co-polymer which comprises heating a homopolymer derived from a compound of the Formula 1a and/or 1b as defined above in the presence of at least one other monomer.

The compounds of the invention may also be used to minimise shrinkage during polymerisation because of their ability to ring open. For example, the compounds of the invention show significant reductions in volume shrinkage when compared with conventional monomers of an equivalent molecular weight. The monomer of the Formula 1a–2 produces a polymer that shrinks only 6.3%. A conventional monomer of the same molecular might would shrink in the order of 11.5%. Such a suppression of volume shrinkage has applications in polymeric coatings, adhesives, dental restorative materials, matrix resins for composites, and fabrication of optical lenses (both contact and conventional).

The bicyclic compounds of the Formula 1b, provide a method of manufacturing crosslinked polymers. They show very little shrinkage on polymerisation due to their high molecular weight and the fact that they are dual ring opening. Thus, they may act as replacements in applications which use conventional di-functional monomers such as CR 39, mono-, di- or tri-ethylene glycol dimethacrylates and BIS-GMA. For example, a common resin system used in dental composites is a mixture of triethyleneglycol dimethacrylate and BIS-GMA. Such a mixture may be replaced with a resin system involving one or more compounds of the Formula 1b, for example, Ib-1, Ib-2, Ib-3 or Ib-4. Similarly, replacement of CR 39 in optical lenses manufactured by a monomer of the Formula 1b may not only result in less polymerisation shrinkage, but the resulting material may have a significantly higher refractive index due to heavy atoms, such as, sulfur in the polymer. Thus, the lenses can be more easily cast and be thinner for a given optical power. An additional advantage of resin systems composed of compounds of the Formula 1a and/or 1b is that they should readily co-polymerise with approximately equal reactivity with other compounds of the Formulae 1a and 1b for a given set of substituents $R^1$ to $R^4$.

In another embodiment the present invention there is provided the use of a compound of the Formula 1a and/or 1b defined above in the manufacture of adhesives, dental composites or optical lenses.

The present invention also provides an adhesive, dental composite or optical lens which is composed wholly or partly of a polymer of co-polymer as defined above.

The present invention further provides a method for the manufacture of an adhesive, dental composite or optical lens which comprises free radical polymerisation of a compound of the Formula 1a and/or 1b as defined above.

The compounds of the invention are stable chemicals and can be kept at room temperature without an inhibitor although preferably they should be refrigerated. They also are stable to mildly acidic or basic conditions and can be prepared from commercially available starting materials. It will be appreciated that a number of possible synthetic routes to the compounds of the invention can be devised in addition to those described herein or in the literature.

Thus, according to another aspect of the present invention there is provided a process for the preparation of a compound of Formula 1a and/or 1b as defined above which comprises reacting 2-chloromethyl-2-propene with a suitable α-ω-dimercapto compound, such as, for example, 1,2-ethanedithiol.

According to a further aspect of the present invention there is provided a process for the preparation of a compound of Formula 1a and/or 1b as defined above which comprises reacting 2-mercaptomethyl-3-mercapto-1-propene with a suitable α-ω-dihalo compound, such as, for example, 1,2-dibromoethane.

Compounds of Formula 1a may also be made from other compounds of Formula 1a, for example, Compound 1a–15 may be made by reacting Compound 1a–4 with methacryloyl chloride.

The present invention also provides a process for the preparation of a compound of Formula 1b as defined above which comprises reacting a compound of Formula 1a as defined above with a suitable difunctional compound, such as, a dichlorodialkylsilane, diisocyanate, dicarboxylic acid or diacid chloride, for example, oxalylchloride.

The invention will now be described with reference to the following Examples. These Examples are not to be construed as limiting the invention in any way.

EXAMPLE 1

Synthesis of 6-methylene-1,4-dithiepane (1a–1)

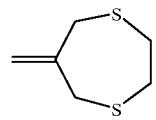

3-Chloro-2-chloromethyl-1-propene (10 g, 80 mmoles) and 1,2-ethanedithiol (7.5 g, 80 mmoles) were made into a 80 mL solution with DMF. This solution was then added via syringe pump over 20 hours to a solution of caesium carbonate (60 g, 180 mmoles) in 250 mL of DMF at 60–70° C. under the protection of a calcium chloride drying tube. After the addition was complete, the reaction was allowed to stir for 24 hours. The reaction was worked up by removing the DMF with a rotary evaporator (ca 50° C.). The residue was titurated with ether a number of times, the ether extracts were dried and evaporated to give 6.6 g of pale oil. The oil was chromatographed on silica gel using hexane:dichloromethane (ca 9:1) to give 3.5 g (30%) clear, foul smelling oil.

$^1$H NMR (CDCl$_3$,): δ3.00 (4H, —SCH$_2$CH$_2$S—), 3.65 (4H, t, J=1.1 Hz, =C—CH$_2$S—), 4.84 (2H, pent, J=1.1 Hz, =CH$_2$).

$^{13}$C NMR (CDCl$_3$): δ38.8 & 38.9 (both —CH$_2$S—), 111.0 (=CH$_2$), 148.2 (quat=C).

$n_D^{20}$=1.5932.

$d^{20}$=1.160 g/cc.

EXAMPLE 2

Synthesis of 3-methylene-1,6-dithiacyclooctane (1a–2)

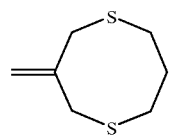

3-methylene-1,6-dithiacyclooctane was synthesised in the same manner as described in Example 1. From 4.0 g of chloro-2-chloromethyl-1-propene, 1.8 g (35%) of purified product was obtained as a clear foul, smelling oil.

1H NMR (CDCl$_3$,): δ1.79 (2H, m, —SCH$_2$CH$_2$CH$_2$S—), 2.88 (4H, m, —SCH$_2$CH$_2$CH$_2$S—), 3.25 (4H, s, =C—CH$_2$S—), 5.20 (2H, s, =CH$_2$).

$^{13}$C NMR (CDCl$_3$): δ29.4 (—SCH$_2$CH$_2$CH$_2$S—), 30.0 (—SCH$_2$CH$_2$CH$_2$S—), 38.0 (=C—CH$_2$S—), 119.3 (=CH$_2$), 145.9 (quat=C).

$n_D^{20}$=1.5842.

$d^{20}$=1.143 g/cc.

EXAMPLE 3

Synthesis of 2-(hydroxymethyl)-6-methylene-1,4-dithiepane (1a–4)

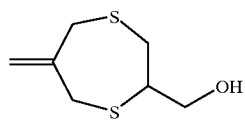

Solution 1. Sodium metal (0.77 g) was dissolved in 35 mL of absolute ethanol at room temperature under nitrogen protection. Then 2,3-dimercapto-1-propanol (1.99 g, 1.6 mL, 16 mmoles) was added dropwise. The solution was taken up in a syringe and diluted to 44 mL. Solution 2. 2-(Chloromethyl)-3-chloro-1-propene (2 g, 16 mmoles) was dissolved in 30 mL of absolute ethanol. The solution was taken up into a syringe and diluted to a volume of 44 mL. Solutions 1 and 2 were added simultaneously (via syringe pump using separate teflon feed lines) to a 40 mL of absolute ethanol at room temperature under nitro:en protection over a period of one hour. After the addition was completed, the reaction was refluxed for one hour. The reaction was then worked up by evaporation of the solvent, dilution with water and extraction with ether. The ether extracts were dried and evaporated to give 2.6 g of oil. The oil was chromatographed on Silica gel using ether:hexane (1:3) to give 1.6 g (57%) of clear oil.

$^1$H NMR (CDCl$_3$): δ2.60–3.80 (9H, mult.), 4.80 (2H, s, =CH$_2$).

$^{13}$C NMR (CDCl$_3$): δ34.5 (—SCH$_2$CH(CH$_2$OH)S—), 39.0 and 40.0 (both=C—CH$_2$S—), 52.8 (—SCH$_2$CH(CH$_2$OH)S—), 53.6 (—CH$_2$OH), 111.8 (=CH$_2$), 147.4 (quat=C).

$d^{20}$=1.236 g/cc.

EXAMPLE 4

Synthesis of 2-(chloromethyl)-6-methylene-1,4-dithiepane (1a–13)

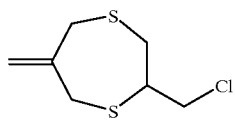

Triphosgene (0.843 g, 2.84 mmoles) was dissolved in 20 mL of dichloromethane. 2-(Hydroxymethyl)-6-methylene-1,4-dithiepane (1.5 g, 8.52 mmoles) and triethyl amine (1.185 mL, 0.86 g) were dissolved in ca. 5 mL of dichloromethane and added dropwise to the triphosgene solution. After ca. one hour the reaction was largely complete. A little more triphosgene was added and the solution was stirred overnight. The reaction was worked up by evaporation of solvent, addition of water and extraction with ether. The extracts were dried and evaporated and the resulting oil was chromatographed on silica gel to give 1.1 g (67%) of clear oil.

$^1$H NMR (CDCl$_3$): δ3.00–4.00 (9H, mult.) 5.20 (2H, s, =CH$_2$).

$^{13}$C NMR (CDCl$_3$): δ34.4 (—SCH$_2$CH(CH$_2$Cl)S—), 39.0 and 40.0 (both=C—CH$_2$S—), 46.0 (—CH$_2$Cl), 49.5 (—SCH$_2$CH(CH$_2$Cl)S—), 112.1 (=CH$_2$), 147.3 (quat=C).

$n_D^{20}$=1.5932.

EXAMPLE 5

Synthesis of 2-(6-methylene-1,4-dithiepane)methyl acetate (1a–14)

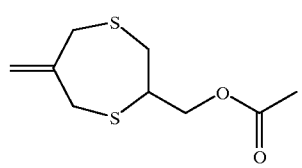

2-(Hydroxymethyl)-6-methylene-1,4-dithiepane (2.0 g, 11.4 mmoles) was dissolved in 10 mL of dichloromethane and triethyl amine (2.4 mL, 1.727 g, 17.1 mmoles) was added to it. The solution was cooled under nitrogen to −10° C., then a solution of acetyl chloride (1.2 mL, 1.34 g, 17.1 mmoles) in dihcloromethane was added dropwise such that the reaction temperature was kept at about −10° C. After the addition was completed, the solution was stirred for ca. 10 minutes and then allowed to warm to room temperature. The reaction was worked up by evaporation of the solvent, addition of water and extraction with ether. The ether extracts were dried and evaporated to give 2.2 g of pale yellow oil. The oil was chromatographed to give 2.0 g (80%) of clear oil.

$^1$H NMR (CDCl$_3$): δ2.00 (3H, s,—CH$_3$), 2.08–3.80 (7H, mult.), 4.1–4.3 (2H, mult, —CH$_2$O—), 4.85 (2H, d, =CH$_2$).

$^{13}$C NMR (CDCl$_3$): δ20.9 (—CH$_3$), 35.1 (—SCH$_2$CH(CH$_2$Cl)S—), 39.0 and 40.3 (both=C—CH$_2$S—), 48.2 (—SCH$_2$CH(CH$_2$O)S—), 65.3 (—CH$_2$O), 111.7 (=CH$_2$), 147.5 (quat=C), 170.5 (C=O).

$n_D^{20}$=1.5500

$D^{20}$=1.223 g/cc.

EXAMPLE 6

Synthesis of 2-(6-methylene-1,4-dithiepane)methyl methacrylate (1a–15)

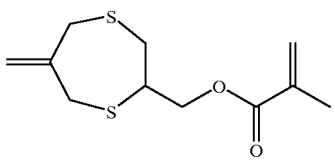

This compound was prepared in an analogous manner to 2-(6-methylene-1,4-dithiepane)methyl acetate (1a–14) of Example 5, using methacryloyl chloride in place of acetyl chloride. 2-(6-Methylene-1,4-dithiepane)methyl methacrylate (1a–15) was obtained in 58% yield.

$^1$H NMR (CDCl$_3$): δ1.90 (3H, s,—CH$_3$), 2.90–3.80 (7H, mult.), 4.1–4.3 (2H, mult, —CH$_2$O—), 4.85 (2H, d, allylic =CH$_2$), 5.60 (1H, s, acrylic =CHH), 6.1 (1H, s, acrylic —CCH).

$^{13}$C NMR (CDCl$_3$): δ18.3 (—CH$_3$), 35.0 (—SCH$_2$CH(CH$_2$O—)S—), 38.7 and 40.2 (both=C—CH$_2$S—), 48.3 (—SCH$_2$CH(CH$_2$O)S—), 65.4 (—CH$_2$O—), 111.6 (allylic =CH$_2$), 126.0 (acrylic =CH$_2$), 135.8 (acrylic quat) 147.5 (allylic quat=C), 168.0 (C=O).

$n_D^{20}$=1.5541

$d^{20}$=1.188 g/cc.

EXAMPLE 7

Synthesis of 2,2-dimethyl-5-methylene-1,3-dithiane (1a–16)

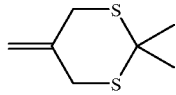

2-(Mercaptomethyl)-3-mercapto-1-propene (Z Chem. 1975, 15, 302)(0.83 g, 6.9 mmoles) and acetone (0.51 mL) were placed in about 15 mL of dichloromethane. Then anhydrous aluminium chloride (0.32 g) was added portion-wise over one minute at room temperature. The solution was stirred at room temperature for 30 minutes. The reaction was worked up by addition of 20 mL of water followed by extraction with dichloromethane. The extracts were dried and evaporated to give 0.89 g clear oil with a penetrating smell. The oil was chromatographed to give 400 mg (40%) of clear oil.

$^1$H NMR (CDCl$_3$): δ1.60 (6H, s, —CH$_3$), 3.35 (—CH$_2$—), 4.90 (4H, s, =CH$_2$).

$^{13}$C NMR (CDCl$_3$): δ30.2 (—CH$_3$), 33.1 (=C—CH$_2$S—), 46.8 (aliphatic quat), 112.0 (=CH$_2$), 139.3 (quat=C).

EXAMPLE 8

Synthesis of dimethyldi-(2-(6-methylene-1,4-dithiepane)methoxy)silane (1b–5)

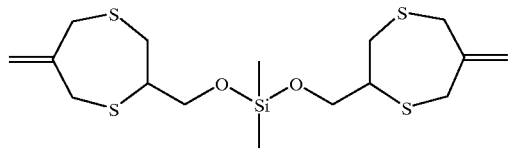

2-(Hydroxymethyl)-6-methylene-1,4-dithiepane (3.0 g, 17.0 mmoles) and triethyl amine (2.7 mL, 1.99 g, 19.7 mmoles) were dissolved in 30 mL of dry dichloromethane and cooled to ca. 0–10° C. under nitrogen protection. Then a solution of dichlorodimethylsilane (1.21 g, 9.38 mmoles) in ca. 5 mL of dichloromethane was added dropwise. After the addition was completed, the reaction was stirred overnight at room temperature. The reaction was worked up by dilution with dichloromethane and washing the solution with water and saturated salt solution. The dichloromethane solution was dried and evaporated to give 3.4 g of clear oil. The oil was chromatographed on silica (80:20 hexane:ether) to give 1.8 g (51%) of clear oil.

$^1$H NMR (CDCl$_3$): δ0.00 (6H, s,—CH$_3$), 2.80–3.80 (18H, mult.), 4.65 (4H, "d" =CH$_2$).

$^{13}$C NMR (CDCl$_3$): δ—3.2 (—CH$_3$), 35.3 (—SCH$_2$CH(CH$_2$O—)S—), 38.9 and 40.0 (both=C). CH$_2$S—), 51.5 (—SCH$_2$CH(CH$_2$O)S—), 64.1 (—CH$_2$O—), 111.3 (=CH$_2$), 147.9 (quat=C).

$d^{20}$=1.182 g/cc.

EXAMPLE 9

Synthesis of di-(2-(6-methylene-1,4-dithiepane) methyl) diglycolylate (1b-6)

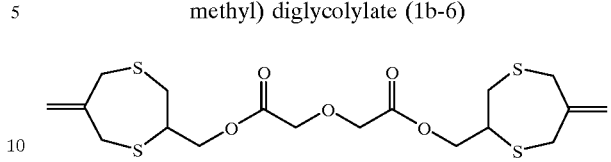

2-(Hydroxymethyl)-6-methylene-1,4-dithiepane (3.0 g, 17.0 mmoles) and triethyl amine (2.6 mL, 1.89 g, 18.7 mmoles) were dissolved in 25 mL of dry dichloromethane and cooled to ca. 0° C. under nitrogen protection. A solution of diglycolyl chloride (1.46 g, 8.52 mmoles) in ca. 5 mL of dichloromethane was then added dropwise. After the addition was completed, the reaction was warmed to room temperature and then refluxed for 2 hours. The reaction was worked up by dilution with dichloromethane and washing the solution with water and saturated salt solution. The dichloromethane solution was dried and evaporated to give 3.6 g of clear oil. The oil was chromatographed on silica (80:20 hexane:ether) to give 1.7 g (44%) of clear oil.

$^1$H NMR (CDCl$_3$): δ2.75–3.70 (14H, mult) 4.1–4.4 (8H, mult, —CH$_2$O—), 4.83 (4H, "d" =CH$_2$).

$^{13}$C NMR (CDCl3): δ34.8 (—SCH$_2$CH(CH$_{2O—)S—)}$, 38.9 and 40.0 (both=C—CH$_2$S—), 47.7 (—SCH$_2$CH(CH$_2$O) S—), 65.4 & 67.9 (both —CH$_2$O—), 111.8 (=CH$_2$), 147.3 (quat=C), 169.2 (C=O).

EXAMPLE 10

Synthesis of di-(2-(6-methylene-1,4-dithiepane) methyl)oxalate (1b–7)

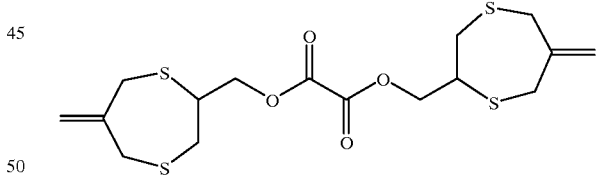

This compound was prepared in the same way as described in Example 9, except oxalyl chloride was used in place of diglycolyl chloride. The product di-(2-(6-methylene-1,4-dithiepane)methyl)oxalate (1b–7) was obtained in 44% yield.

$^1$H NMR (CDCl$_3$): δ2.75–3.70 (14H, mult) 4.1–4.4 (4H, mult, —CH$_2$O—), 4.88 (4H, "d" =CH$_2$).

$^{13}$C NMR (CDCl$_3$): δ34.6 (—SCH$_2$CH(CH$_2$O—)S—), 39.1 and 39.8 (both=C—CH$_2$S—), 46.7 (—SCH$_2$CH (CH$_2$O—)S—), 67.3 (—CH$_2$O—), 112.1 (=CH$_2$) 147.0 (quat=C), 156.2 (C=O).

EXAMPLE 11

Synthesis of di-(2-(6-methylene-1,4-dithiepane) methyl) sebacate (1b–8)

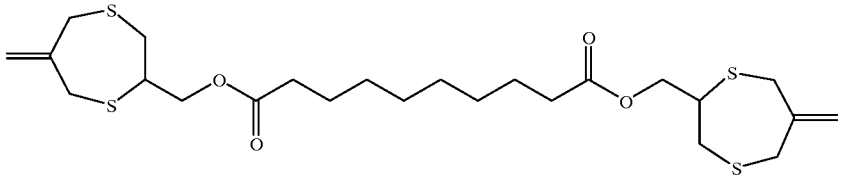

This compound was prepared in the same way as described in Example 9, except sebacoyl chloride was used in place of diglycolyl chloride. The product di-(2-(6-methylene-1,4-dithiepane)methyl) sebacate was obtained in 36% yield.

$^1$H NMR (CDCl$_3$): δ1.2 (8H, br.s.), 1.55 (4H, br.s.), 2.20 (4H, "t", —CH$_2$—OC=O—), 2.75–3.70 (14H, mult), 4.1–4.4 (4H, mult., —CH$_2$O—), 4.79 (4H, "d" =CH$_2$).

$^{13}$C NMR (CDCl$_3$): δ24.8, 29.0, 34.0, 35.0, 38.9 and 40.2 (both=C—CH$_2$S—), 48.2 (—SCH$_2$CH(CH$_2$O—)S—), 64.9 (—CH$_2$O—), 111.6 (=CH$_2$), 147.4 (quat=C), 1.73.2 (C=O). mp 56–8° C.

EXAMPLE 12

Synthesis of di-(2-(methylene-1,4-dithiepane) methyl)phthalate (1b–9)

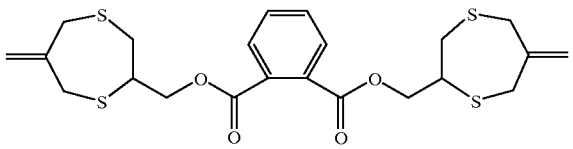

2-(Hydroxymethyl)-6-methylene-1,4-dithiepane (4.0 g, 22.7 mmoles) and triethyl amine (3.5 mL, 2.52 g, 25.0 mmoles) were dissolved in 15 mL of dry dichloromethane under nitrogen protection. Phthaloyl chloride (2.3 g, 11.4 mmoles) in ca. 5 mL of dichloromethane was then added dropwise to the solution. After the addition was completed, the solution was refluxed for 2 hours, and then stirred overnight at room temperature. The reaction was worked up by dilution with dichloromethane, washing with water and dilute sulfuric acid (2 M), dried and evaporated to give 5.1 g of pale orange oil. The oil was chromatographed on silica with dichloromethane to give 2.7 g (49%) of oil.

$^1$H NMR (CDCl$_3$): δ2.75–3.70 (14H, mult.) 4.2–4.6 (4H, mult. —CH$_2$O—), 4.85 (4H, "d" =CH$_2$), 7.55 (2H, mult, aromatic), 7.73 (2H, mult, aromatic).

$^{13}$C NMR (CDCl$_3$): δ35.0 (—SCH$_2$CH(CH$_2$O—)S—), 39.0 and 40.2 (both=C—CH$_2$S—), 47.9 (—SCH$_2$CH(CH$_2$O—)S—), 66.4 (—CH$_2$O—), 111.8 (=CH$_2$), 129.0 (aromatic), 131.4 (aromatic), 131.7 (quat. aromatic), 147.3 (quat=C), 166.9 (C=O).

EXAMPLE 13

Synthesis of di-(2-(6-methylene-1,4-dithiepane) methyl) terephthalate (1b–10)

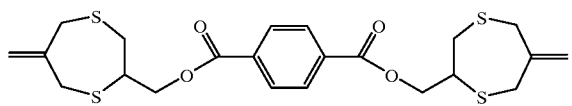

This compound was made in the same manner as described in Example 12 except that terephthaloyl chloride was used in place of phthaloyl chloride. The yield of di-(2-(6-methylene-1,4-dithiepane)methyl) terephthalate (1b–10) was 37%.

$^1$H NMR (CDCl$_3$): δ2.75–3.70 (14H, mult.) 4.2–4.6 (4H, mult. —CH$_2$O—), 4.90 (4H, "d" =CH$_2$), 8.05 (4H, s. aromatic).

$^{13}$C NMR (CDCl$_3$): δ35.1 (—SCH$_2$CH(CH$_2$O—)S—), 39.0 and 40.3 (both=C—CH$_2$S—), 48.2 (—SCH$_2$CH (CH$_2$O—)S—), 66.1 (—CH$_2$O—), 111.9 (=CH$_2$), 129.8 (aromatic), 133.8 (quat. aromatic), 147.4 (quat=C), 165.2 (C=O). mp. 103–5° C.

EXAMPLE 14

Synthesis of di-(2'-(6'-methylene-1', 4'-dithiepane) methyl) 1,6-hexanediylbis[carbamate] (1b–11)

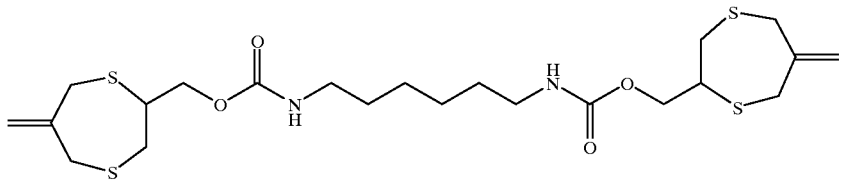

2-(Hydroxymethyl)-6-methylene-1,4-dithiepane (2.0 g, 11.4 mmoles) was dissolved in 10–15 mL of dichloromethane under nitrogen protection. 1,6-diisocyanatohexane (0.95 g, 5.68 mmoles) in 3 mL of dichloromethane was added dropwise with stirring. A trace amount of stannous octoate was added to the solution. The reaction was stirred overnight at room temperature. The reaction was worked up by evaporating the solvent and chromatographing the white residue on silica to give 2.0 g (69%) of white solid.

$^1$NMR (CDCl$_3$): δ1.2 (12H, br.d), 2.75–3.70 (14H, mult), 4.0–4.3 (4H, mult, —CH$_2$O—), 4.90 (4H, "d" =CH$_2$), 5.0 (2H, br.s,.NH).

$^{13}$C NMR (CDCl$_3$): δ26.1, 29.7, 35.1 (—SCH$_2$CH(CH$_2$O—)S—), 38.8 and 40.2 (both =CH$_2$S—), 40.8 (NH—CH$_2$—), 48.9 (—SCH$_2$CH(CH$_2$O—)S—), 65.5 (—CH$_2$O—), 111.5 (=CH$_2$), 147.5 (quat=C), 1.56 (C=O).

mp 89–91° C.

ECAMPLE 15

Synthesis of di-(2'-(6'-methylene-1,4-dithiepane)methyl) (methylenedi-1,4-phenylene)bis[carbamate] (1b–12)

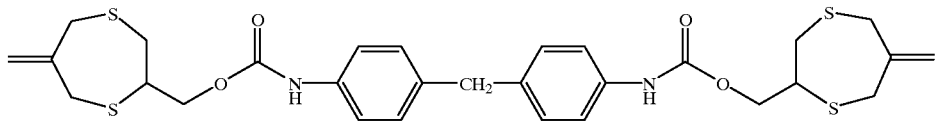

2-(Hydroxymethyl)-6-methylene-1,4-dithiepane (2.6 g, 14.8 mmoles) was dissolved in 20 mL of dichloromethane under nitrogen protection and a small amount of stannous octoate was added. A solution of 4,4'-methylenebis(phenyl isocyanate) (1.85 g, 7.4 mmoles) in dichloromethane was then added dropwise to the solution. The reaction was stirred overnight at room temperature. The solvent was evaporated, and the mixture was dissolved as much as possible in boiling chloroform and then filtered. The chloroform filtrate was evaporated to give a clear rubbery solid that went white and hardened overnight to a white solid.

$^1$H NMR (CDCl$_3$): δ2.75–3.70 (14H, mult), 4.90 (2H, s, phenyl-CH$_2$-phenyl), 4.2–4.6 (4H, mult, —CH$_2$O—), 4.90 (4H, "d" =CH$_2$), 6.7 (br.s, NH), 7.0–7.3 (8H, mult, aromatic).

EXAMPLE 16

Preparation of Homopolymer of 6-methylene-1,4-dithiepane (1a–1)

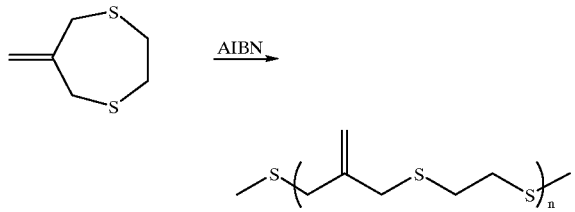

AIBN (8.8 mg, 0.05 mmole) was dissolved as much as possible in neat 6-methylene-1,4-ditheipane (0.4616 g, 3.16 mmole). The mixture was transferred to a small polymerisation tube and freeze-thaw degassed under vacuum a number of times. The tube was then sealed under vacuum by flame. The sample was polymerised at 70° C. for about 20 hours. It was apparent that polymerisation was very rapid as a white solid formed within about 15–20 minutes of heating.

After 20 hours of heating, the tube was cooled, opened and the polymer was removed as a solid white block. The material is highly insoluble in any solvent at room temperature, however it was slightly soluble in DMSO or pyridine at 90° C. enabling characterisation by NMR spectroscopy. High temperature GPC analysis (135° C., trichlorobenzene) revealed the Mw was 687 000 g with a dispersity of 3.8. This magnitude of molecular weight was consistent with its NMR spectra It is apparent that the molecular weight is quite high as there is no trace of signals from end groups (i.e. no methyl groups from AIBN initiation, NC—C(CH$_3$)$_2$—). The polymer seemed to be highly crystalline and showed a sharp melting point transition at 129° C. A small glass transition was observed at −35° C. At the melting point, the material went from white opaque solid to a crystal-clear solid.

$^1$H NMR (DMSO-d$_6$, 90° C., 250 MHz) δ2.65 (4H, —SCH$_2$CH$_2$S—), 3.30 (4H, =C—CH$_2$S—), 5.08 (2H, =CH$_2$). $^{13}$C NMR (DMSO-d$_6$, 90° C.) δ30.7 & 34.9 (both —CH$_2$S—), 114.7 (=CH2), 141.1 (quat=C).

d$^{20}$=1.26–7 g/cc.

Volume shrinkage during polymerisation=8.0–8.8%. Expected shrinkage of monomer of MW 148 g/mole is ca 12.3%.

EXAMPLE 17

Preparation of Homopolymer of 3-methylene-1,6-dithiacyclooctane (1a–2)

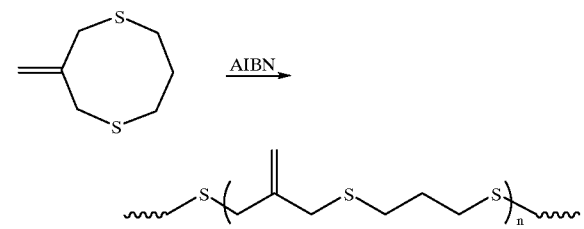

The homopolymer of 3-methylene-1,6-dithiacyclooctane was prepared in the same manner as described in Example 16. A white solid showed greater toughness than the homopolymer of 6-methylene-1,4-dithiepane. The material was highly insoluble in any solvent at room temperature. It appeared to be very lightly cross linked as it greatly swelled in hot pyridine with little observable dissolution. High temperature GPC analysis (135° C., trichlorobenzene) revealed the Mw was 486 000 g with a dispersity of 3.8. As the polymer is lightly cross linked this figure is presumably due to extractable, non-cross linked polymer. This magnitude of molecular weight was consistent with its NMR spectra. It is apparent that the molecular weight is quite high as there is no trace of signals from end groups (i.e. no methyl groups from AIBN initiation, NC—C(CH$_3$)$_2$—). The polymer seemed to be highly crystalline and showed a sharp melting point transition at 99.5° C. A small glass transition was observed at −45° C. At the melting point, the material went from white opaque solid to crystal-clear solid.

$^1$H NMR (pyridine-d$_5$, 90° C., 250 MHz) δ2.00 (2H, p, J=7.1 Hz, —SCH$_2$CH$_2$CH$_2$S—), 2.75 (4H, t, J=7.1 Hz, —SCH$_2$CH$_2$CH$_2$S—), 3.45 (4H, =C—Ch$_2$S—), 5.18 (2H, =CH$_2$). $^{13}$C NMR (pyridine-d$_5$, 90° C.) δ29.4 (—SCH$_2$CH$_2$CH$_2$S—) 30.8 (—SCH$_2$CH$_2$CH$_2$S—), 36.2 (=C—CH$_2$S—), 114.8 (=CH$_2$), 142.3 (quat=C).

d$^{20}$=1.213 g/cc.

Volume shrinkage during polymerization=6.3%. Expected shrinkage of a monomer of molecular weight of 160 g/mole is ca. 11.5%.

EXAMPLE 18

Preparation of Co-polymer of 6-methylene-1,4-dithiepane (1a-1) and 3-methylene-1,6-dithiacyclooctane (1a–2)

AIBN (3.6 mg, 0.043 mmole) was dissolved in a mixture of 6-methylene-1,4-dithiepane (192.2 mg, 165.7 μl, 1.30 mmole) and 3-methylene-1,6-dithiacyclooctane (207.8 mg, 182.8 μl, 1.30 mmole) in a small polymerisation tube. The mixture was freeze-thaw degassed a number of times under vacuum before finally being flame sealed. The sample was polymerised at 70° C. for 2.5 days. A clear polymer formed in the tube. When the sample was cooled, the polymer turned white (crystallised). The material was firm but rubbery and showed a glass transition at −47.5° C. and a melting point at 53.3° C. $^1$H NMR (pyridine-d$_5$, 90° C., 250 MHz) δ1.95 (2H, p, J=7.0 Hz, —SCH$_2$CH$_2$CH$_2$S—), 2.70 (4H,t, J=7.0 Hz, —SCH$_2$CH$_2$CH$_2$S—), 2.86 (4H, s, —SCH$_2$CH$_2$S—), 3.48 & 3.52 (both 4H, s, =C—CH$_2$S—), 5.18 (4H, s, =CH$_2$). $^{13}$C NMR (CDCl$_3$, 25° C.) δ28.4 (—SCH$_2$CH$_2$CH$_2$S—), 30.3 & 30.8 (both —SCH$_2$—), 35.4 & 35.6 (both=C—CH$_2$S—), 115.6 & 115.8 & 116.0 (all=CH$_2$), 140.8 (quat=C).

$^{20}$=1.202 g/cc.

Density of mixture of two monomers=(146+160)/(126+140)=1.150 g/mL. Volume shrinkage during polymerisation=(1.202−1.150)/1.202×100%=4.3%. Expected shrinkage of a monomer of molecular weight of (148+160)/2=154 g/mole is ca. 12%.

EXAMPLE 19

Preparation of Co-polymer of 6-methylene-1,4-dithiepane (1a–1) and Methyl Methacrylate A 0.5 mL solution of azobisisonitrile (0.05 M, 4.1 mg), 6-methylene-1,4-dithiepane (0.5 M, 36.5 mg), inhibitor free methyl methacrylate (2.5 M, 125 mg) and non-deuterated benzene (0.21 mmoles, 19 mL) in benzene-d$_6$ was placed in a thick walled NMR tube, freeze thaw degassed under vacuum, and sealed. The sample was polymerised at 70° C. for 148 minutes and the extent of polymerisation was monitored by $^1$H NMR spectroscopy. During this time, both monomers were consumed. At the end of the polymerisation, conversion of the methyl methacrylate was 80% and the dithiepane 39%. A small portion of the contents of the NMR tube was examined by gel permeation chromatography (GPC) using a Water Instrument connected to six μ-styragel columns (10$^6$, 10$^5$, 10$^4$, 10$^3$, 500 and 100 Å pore size). Tetrahydrofuran was used as eluent at a flow of 1 mL/min and the system was calibrated using narrow distribution polystyrene standards (Waters). The number average weight was 17 539 and weight average molecular weight was 35 589. Analysis of the conversion/monomer feed composition using the integrated form of the co-polymer equation gave the reactivity ratios of MMA and dithiepane to be 3.2±0.3 and 0.27±0.05, respectively.

The remaining contents of the tube were poured into methanol and the precipitated co-polymer was collected and freeze dried. The co-polymer was analysed by $^1$H and $^{13}$C NMR spectroscopy. In addition to poly-MMA signals, vinylic signals at 4.7–9 ppm in the $^1$H NMR spectrum were evidence of the ring-opened repeat unit from the dithiepane in the co-polymer. The ratio of the ring opened unit to MMA in the polymer was ca 1:16. The $^{13}$C NMR spectrum showed signals at δ140 (quat=C), 118 & 116 (=CH$_2$) 38.8, 35.4, 33.4, 30.4 (all —CH$_2$S—) ppm as evidence of the ring opened repeating unit in the co-polymer.

EXAMPLE 20

Homopolymerisation of Functionalised Monomers

The monomers listed in the table below were thermally polymerised in bulk using AIBN as an initiator as described in Examples 16, 17 and 18. Molecular weight was determined by ambient temperature GPC using polystyrene standards.

| Monomer | Polymer | Conversion | Mw | Dispersity | Density (g/cm$^3$) |
|---|---|---|---|---|---|
| 1a-4 | gum | low | 40 000 | 3.0 | — |
| 1a-13 | gum | 70% | 80 000 | 3.3 | — |
| 1a-14 | gum | 60% | 63 500 | 2.1 | — |
| 1a-15 | transparent hard solid | ca. 100% | cross linked | | 1.278 (7% shrinkage) |

EXAMPLE 21

Photopolymerisation of Monomers

Samples were prepared by addition of ca. 0.3% photoinitiator ("Darocur 1173" by Ciba-Giegy) to the bulk monomer (s) (ca. 200 mg) and then irradiated by 350 nm light at an intensity of 0.15 mW/cm$^2$ for 3 hours.

| Monomer | Polymer | Polymer Density g/cm$^3$ (Polymerisation Shrinkage) |
|---|---|---|
| 1a-1 | white hard solid | 1.27 (8.5%) |
| 1a-2 | white hard solid | 1.229 (7.0%) |
| 1a-14 | transparent sticky gum | — |
| 1a-15 | transparent hard solid | 1.282 (7.3%) |
| 1b-5 | transparent elastic solid | 1.223 (3.3%) |
| 1a-1 + 1a-2 (1:1) copolymer | pale yellow, rubbery, solid | 1.214 (5.2%) |

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

What is claimed is:
1. A compound having a formula which is:
1a-4 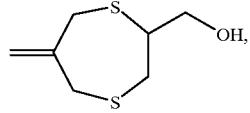
1a-5 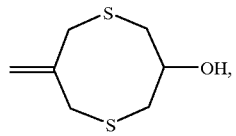
1a-7 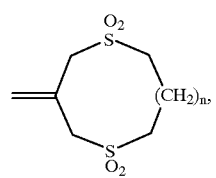
1a-8 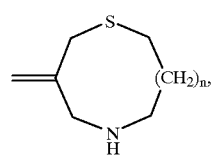
1a-9 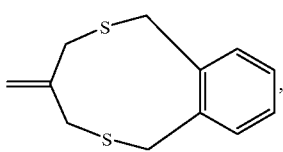
1a-11 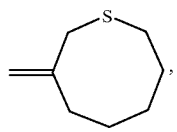
1a-12 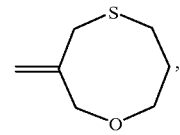
1a-13 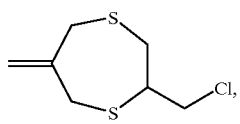
1a-14 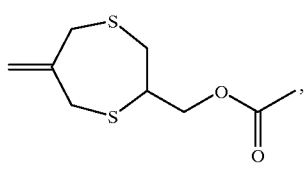
1a-15 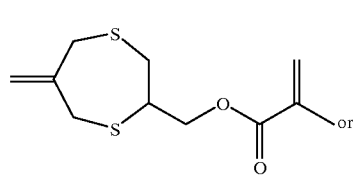
1a-16 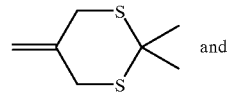 and 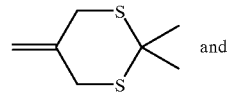
wherein n is an integer including 0.
* * * * *